United States Patent [19]

Breslin

[11] Patent Number: 5,474,685
[45] Date of Patent: Dec. 12, 1995

[54] APPARATUS AND METHOD FOR DETECTING AND RECOVERING IMMISCIBLE LIQUIDS OF DIFFERENT DENSITIES

[76] Inventor: Michael K. Breslin, 149 Shelley Dr., Mill Valley, Calif. 94941

[21] Appl. No.: 194,994

[22] Filed: Feb. 14, 1994

[51] Int. Cl.⁶ ............................. B01D 17/12; E21B 44/00
[52] U.S. Cl. .................... 210/741; 166/53; 210/121; 210/170; 210/242.3; 210/747; 210/776
[58] Field of Search ..................... 210/86, 90, 104, 210/121, 122, 242.1, 242.3, 170, 741, 744, 747, 776, 923, 321, 65, 651; 166/53, 265; 417/36, 61; 73/439, 299

[56] References Cited

U.S. PATENT DOCUMENTS

| | | | |
|---|---|---|---|
| 3,603,952 | 9/1971 | Smith | 340/224 |
| 3,719,936 | 3/1973 | Daniels | 340/236 |
| 4,131,773 | 12/1978 | Maham | 200/61.05 |
| 4,243,529 | 6/1979 | Strauss | 210/923 |
| 4,434,650 | 3/1984 | Perry | 73/61.51 |
| 4,469,170 | 9/1984 | Farmer, Jr. | 166/53 |
| 4,497,370 | 2/1985 | Breslin | 166/372 |
| 4,527,633 | 7/1985 | McLaughlin | 166/370 |
| 4,546,830 | 10/1985 | McLaughlin | 166/370 |
| 4,549,171 | 10/1985 | Akiba | 340/605 |
| 4,625,801 | 12/1986 | McLaughlin | 166/267 |
| 4,663,037 | 5/1987 | Breslin | 210/170 |
| 4,678,040 | 7/1987 | McLaughlin | 166/370 |
| 4,761,225 | 8/1988 | Breslin | 210/104 |
| 5,028,212 | 7/1991 | Brophey et al. | 417/36 |
| 5,180,013 | 1/1993 | Abdul | 166/53 |
| 5,207,897 | 5/1993 | Baird | 210/109 |
| 5,316,085 | 5/1994 | Dawson | 166/53 |
| 5,341,877 | 8/1994 | Abdul et al. | 166/53 |

*Primary Examiner*—Joseph W. Drodge
*Attorney, Agent, or Firm*—Townsend and Townsend and Crew

[57] ABSTRACT

A float (26) resides at an interface (21) between a first liquid (20) floating on another liquid (22). A pneumatic pressure sensor (32) senses back-pressure at the float (26) via a conduit (30) and a bubbler hole, or pressure sensing point (28) and relays the information to a recorder (37). Also, a combination detection and recovery device employs the above detection device coupled with a floating liquid skimming device. The recovery unit (90) of the skimming device has a bubbler hole (168) connected to pressure sensor (32) via conduit (30). The pressure sensor (32) is then connected to a pump (88) via another conduit (38). When the pressure at the bubbler hole (168) reaches a predetermined value corresponding to a given fluid thickness, the sensor (32) activates the pump (88) which moves the floating liquid (20) from the recovery unit (90) to a fluid receptacle (102). The apparatus is adapted for use inside of well casings (50) as well as for liquids (22) with larger surface areas, such as fluid storage tanks, lakes, and streams. The float (97) can be constructed employing a semipermeable membrane (110) which allows one liquid to enter and excludes the other.

8 Claims, 6 Drawing Sheets

APPARATUS AND METHOD FOR DETECTING AND RECOVERING IMMISCIBLE LIQUIDS OF DIFFERENT DENSITIES

BACKGROUND—CROSS REFERENCES TO RELATED APPLICATIONS

My previous patents which relate to the present invention include U.S. Pat. No. 4,497,370, Feb. 5, 1985, entitled "Apparatus And Method For Recovery Of Liquid Hydrocarbons From Ground Water," U.S. Pat. No. 4,663,037, May 5, 1987, entitled "Apparatus For Recovery Of Liquid Hydrocarbons From Ground Water," and U.S. Pat. No. 4,761,225, Aug. 2, 1988, entitled "Apparatus For Controlling The Removal Of Liquid Hydrocarbons From Groundwater."

BACKGROUND—FIELD OF INVENTION

This invention relates to detecting the presence and recovery of a liquid floating on a submerged liquid, such as a liquid hydrocarbon floating on ground water or of a liquid submerged below a floating liquid, such as a heavier-than-water oil submerged under water.

BACKGROUND—DISCUSSION OF PRIOR ART

Proposals have been made to recover a liquid floating on another liquid. For example, when oil spills onto a body of water, there is a need to remove the oil from atop the water. One device for removing the floating liquid operates on the principle of specific gravity. This recovery device, shown in my above U.S. Pat. No. 4,663,037, has a specific gravity such that it floats on the submerged liquid and sinks in the floating liquid; thus the floating liquid and submerged liquid interface is never above the top of the recovery device. An inlet for recovering the floating liquid is located on the upper portion of the recovery device; this allows the floating liquid, when present, to enter the recovery device. Additionally, the inlet position also prevents the submerged liquid from entering the recovery device. A pump is used to move the collected floating liquid to a fluid receiver.

The above device has been manufactured by this inventor incorporating a pneumatic sensor outside the floating inlet to detect the presence of a liquid floating upon another heavier liquid and to turn on a pump when such floating liquid reached a certain thickness. The proposed invention improves upon the device by adding a recorder and in another imbodiment detects liquid inside the floating intake and is thus more accurate in its detection and recovery of lighter-phase liquids and interferes less with the surrounding environment.

Another floating liquid recovery device, disclosed in my above U.S. Pat. No. 4,497,370, uses a selective membrane which allows the floating liquid to pass while blocking the submerged liquid. This device positions itself at or above the floating liquid-submerged liquid interface. A pump is then used to move the collected floating liquid to a fluid receiver.

The pumps for these two recovery systems operate either continuously or on a timing system, rather than on a need basis, i.e., only when floating liquids are present. Thus pumps often pump dry, making the system inefficient. Also, if the area holds harmful vapors, the pumps will expel harmful vapors to the atmosphere.

Another underground oil spill recovery system is currently being sold by Oil Recovery Systems of Greenville, N.H. The system uses a floating oil recovery unit comprised of a receptacle for receiving the oil and a semipermeable membrane on the periphery of the receptacle. The membrane is submerged into the water so that all hydrocarbons on the water will contact the membrane. As the receptacle is filled by the hydrocarbons, which pass through the membrane, a float inside the receptacle rises and triggers a switch that activates a pump which empties the receptacle. This system depends upon the semipermeable membrane to separate the oil from the water. Such an oil recovery system is disclosed in U.S. Pat. No. 4,243,529 to Strauss, issued Jan. 6, 1981.

A floating liquid detection and skimming device is disclosed in U.S. Pat. No. 4,469,170 to Farmer (1984). The device includes a float adapted to float in a two-liquid body. A skirt receptacle is connected to the float. One end of receptacle has openings for collecting hydrocarbon liquid. Spaced-apart sensors attached to the receptacle sense the hydrocarbon-water interface and activate a pump for removing the hydrocarbon liquid from the receptacle in response to the level of hydrocarbon-water interface.

The detection part of this device is electrical. It uses the conducting property of water and the non-conducting property of oil for finding the oil-water interface. Thus this device will recover a floating liquid only if it is non-conducting and the submerged liquid is conducting. Since electronic devices are located inside the detection unit, the chance of a fire or an explosion is increased.

An oil recovery system is disclosed in my above U.S. Pat. No. 4,761,225 in which a floating liquid recovery device is coupled with a pumping device. A pressure sensor measures pressure changes associated with an increase in fluids and then activates a pump to remove water. This skimmer and pump system operates pneumatically.

Although this device detects a change in fluid thickness, it does not differentiate between the floating liquid and the submerged liquid. More specifically, it does not detect changes in thickness of the floating liquid independent of depth changes in the submerged liquid. The detection device only activates a water draw-down pump which removes only the submerged liquid, i.e., water. Only the submerged liquid is removed because the pump inlet is located below the liquid hydrocarbon-water interface.

An oil spillage detection system described in U.S. Pat. No. 3,719,936 to Daniels (1973) resides partially submerged in a body of water. A selectively transmissive member is located inside the housing at the oil-water interface. Oil, but not water, is transmitted through the member to a chamber inside the housing which includes a sensor for detecting the presence of oil. The sensor is typically an electrical Resistance-Temperature-Dependent (RTD) type sensor.

The electronic devices located inside this detection unit increase the chance of fire due to the presence of electronic circuitry. In this device, oil is only detected; other than small samples, it is not recovered. This device can only take limited numbers of measurements. In addition, this device requires regular maintenance; it must be recovered from the site to check samples and it must be cleaned frequently.

Many liquid hydrocarbon detection devices utilize electrical sensor devices mounted on floats. Devices of this type are disclosed in U.S. Pat. No. 4,131,773 to Maham (1978), U.S. Pat. No. 4,434,650 to Perry (1984), and U.S. Pat. No. 4,549,171 to Akiba (1985).

As stated before, an electronic sensor system increases the risk of fire and explosion. In addition, these three devices detect only oil; they cannot recover it. Most electrically controlled oil detection devices are dependent upon the non-conducting property of oil and conducting property of water; thus the success of these types of devices is limited to the aforementioned conditions.

OBJECTS AND ADVANTAGES

Accordingly, several objects and advantages of the present invention are to provide an improved floating oil recovery device which (a) is easy to transport, install, and operate;

(b) is cost effective to install and operate;

(c) requires little maintenance and no operator supervision;

(d) operates properly and continuously without interruption in process regardless of fluid level fluctuations;

(e) has a flexible design for multiple uses (i.e., small and large diameter wells, tanks, lakes, etc.);

(f) actuates other devices such as visual indicators, audible indicators, or recovery unit pumps upon detecting floating liquid;

(g) is not limited to oil and water applications or conditions where floating liquid is non-conductive and submerged liquid is conductive;

(h) operates only when floating liquids are present, thus minimizing expulsion of harmful vapors into the atmosphere, increasing recovery system efficiency, and permitting operation in remote areas; and (i) eliminates the possibility of fire or explosion due to electronic circuitry; and (j) does not encourage the growth of bacteria at an oil/water interface due to injection of oxygen into the liquids.

Further objects and advantages are to provide a floating liquid detection device which can be coupled with any type of floating liquid recovery system for enhancing system performance. Additionally, a plurality of bubbler holes and conduits can be connected to the pneumatic pressure sensor as backups to ensure proper operation. Alternatively, a plurality of bubbler holes, conduits, and sensors can be used for actuating signaling device or pumping unit. Still further objects and advantages will become apparent from a consideration of the ensuing descriptions and accompanying drawings.

DESCRIPTION OF DRAWINGS

FIG. 3 shows another version of the device of FIG. 2, but adapted for use inside a well casing.

FIG. 3-A shows the top view of the recovery unit of FIG. 3.

FIG. 3-B shows the side view of the recovery unit of FIG. 3.

FIG. 5-A shows a broken-out view of the recovery unit shown in FIG. 5.

FIG. 5-B shows a broken-out view of another version of the recovery unit of FIG. 5-A, but having bubbler hole-floating liquid interface below selective membrane housing and internal to a conduit which holds the floating liquid.

FIG. 5-C shows a broken-out view of another version of the recovery unit of FIG. 5-A, but having bubbler hole-floating liquid interface below the recovery unit and internal to a conduit which holds the floating liquid.

REFERENCE NUMERALS

14 Mechanical Fitting (Connects Conduits 30 and 31)
16 Mechanical Fitting (Tee Fitting)
18 Mechanical Fitting
20 Floating Liquid
21 Floating Liquid-Submerged Liquid Interface
22 Submerged Liquid
23 Mechanical Fitting
24 Air (Atmosphere)
25 Tee Fitting
26 Float Device
27 Bore Hole Through Float Device
28 Bubbler Hole (or Pressure Sensing Point)
29 Bubbler Hole (or Pressure Sensing Point)
30 Conduit (Conduit Connecting Bubbler Hole and Sensor)
31 Conduit (Coiled & Connecting Bubbler Hole & Sensor)
32 Pneumatic Sensor
33 Compressed Air (Low Pressure)
34 Compressed Air (High Pressure)
35 Alarm
36 Signaling Device
37 Recording Device
38 Conduit For Carrying High Pressure Air From Sensor
50 Well Casing
52 Well Casing Perforations
54 Rigid Conduit
56 Disk Spacer
58 Float Device for Well Casing
60 Bore Hole
62 Conduit
63 Conduit
64 Mechanical Fitting (Connects Disk Spacer to Conduit)
65 Mechanical Fitting (Connects Disk Spacer to Conduit)
66 Mechanical Fitting/Check Valve
69 Screen
80 Inlet for Recovering Floating Liquid
81 Vertical Bore Hole for Carrying Floating Liquid
82 Outlet
83 Conduit
84 Discharge Conduit (Holds Floating Liquid)
86 Mechanical Fitting/Check Valve
88 Pump Device (for Floating Liquid)

90 Float/Specific Gravity Recovery Unit
92 Selective Membrane Recovery Unit Adapted for Well Casing
93 Selective Membrane Recovery Unit Adapted for Well Casing
95 Float/Specific Gravity Recovery Unit Adapted For Well Casing
96 Selective Membrane Recovery Unit Adapted for Well Casing
97 Selective Membrane Recovery Unit
98 Particle Screen
100 Floatation Material
102 Floating Liquid Receiver
110 Selective Membrane
112 Chamber Formed By Selective Screen
146 Mechanical Fitting (Plug)
148 Mechanical Fitting (Plug)
150 Mechanical Fitting
151 Mechanical Fitting (Hose Barb)
152 Mechanical Fitting (Plug)
153 Mechanical Fitting (Hose Barb)
154 Mechanical Fitting (Plug)
156 Mechanical Fitting (Hose Barb)
160 Vertical Bore Hole which Hold Compressed Air
162 Conduit
168 Bubbler Hole
170 Bubbler Hole
180 Bubbler Hole
182 Mechanical Fitting (T-joint)
183 Bubbler Hole
184 Conduit-Carries Floating Liquid from Recovery Device to Pump
186 Conduit-Carries Floating Liquid from Pump Unit to Receiver
190 Mechanical Fitting (Connects Conduit to Pump)
192 Mechanical Fitting (Connects Conduit to Pump)
194 Mechanical Fitting (Connects Conduits)
196 Weight (Slides On Conduit 84)

SUMMARY

In accordance with the invention, a device for recovering one liquid floating on another comprises a float, a bubbler hole, a pneumatic sensor, and a conduit connecting the bubbler hole to the pneumatic sensor.

Figure 1:
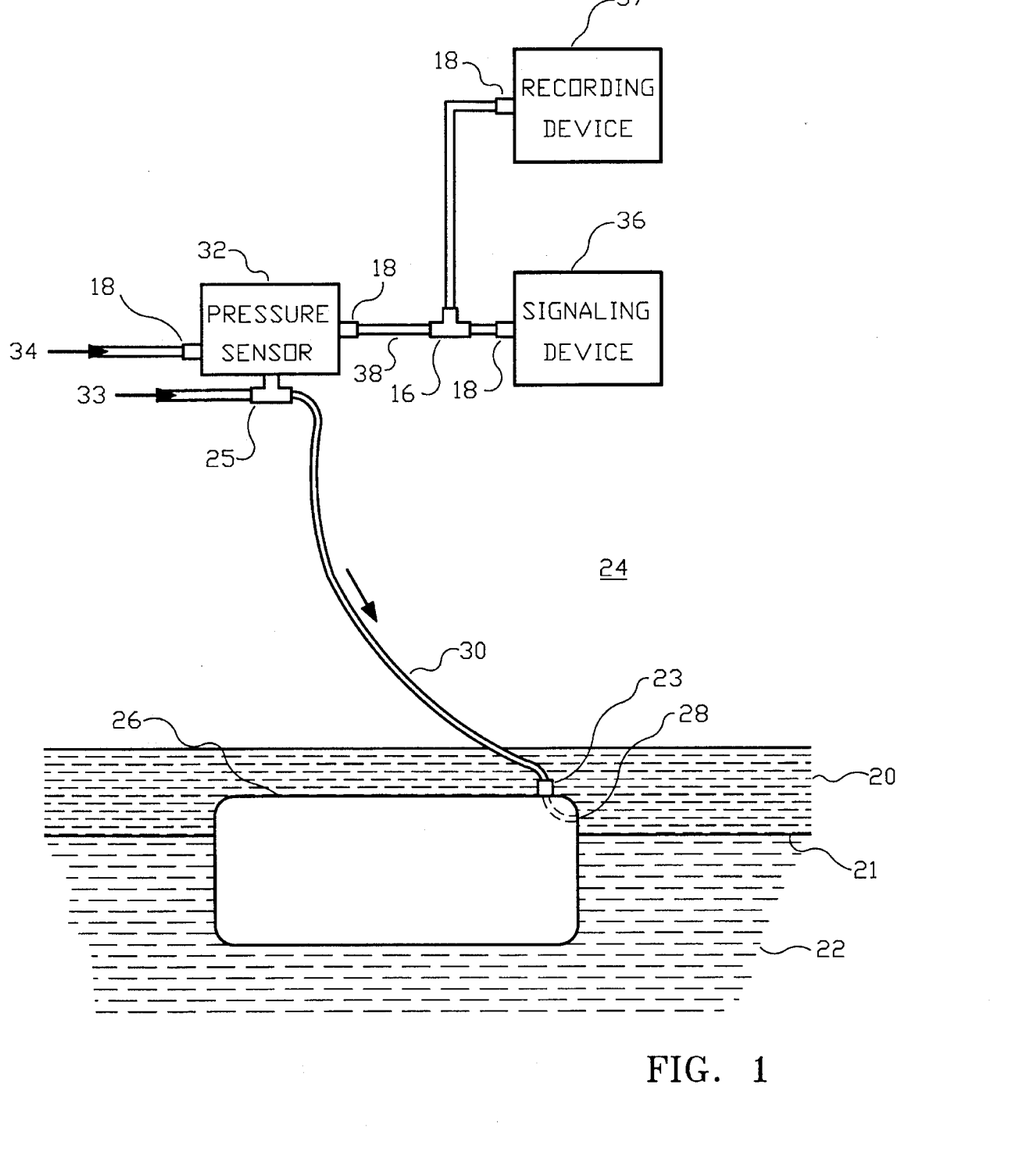
FIG. 1 is a diagram of a floating liquid detection device in accordance with the invention with an information recording device coupled to the sensing device.

DESCRIPTION/OPERATION—FIG. 1

In a first embodiment, shown in FIG. 1, a float of a floating liquid detection device resides at an interface 21 of two unmixed liquids, i.e., an oil-water interface. The device includes float 26 which has an average specific gravity greater than that of floating liquid 20 and less than that of submerged liquid 22; thus it resides at interface 21 of floating liquid 20 and submerged liquid 22. Liquid 20 may be oil which has spilled onto liquid 22, which may be a body of water, such as a bay or pond.

A bubbler hole or orifice 28 which emits a steady flow of fluid, usually air, is attached to float 26 and communicates with floating liquid 20. Bubbler holes can vary in size; bubbler hole 28 is approximately 2.8 mm (⅛ of an inch) in diameter.

Bubbler hole 28 is connected to one end of a conduit 30 via a mechanical fitting 23. The other end of conduit 30 is connected to a source of compressed air 33 and a pressure sensor 32 via a tee fitting 25. Compressed air 33, which is emitted constantly at a low rate, travels through conduit 30 to bubbler hole 28. Another conduit 38 is connected to pressure sensor 32 via a mechanical fitting 18. A signaling device 36 is connected to the other end of conduit 38 via mechanical fitting 18. An information recording device 37 is connected to both the signaling device 36 and the pressure sensor 32 via a tee fitting 16 in conduit 38. The information on the thickness of floating liquid 20 can be recorded in several ways, e.g. on paper (e.g., ticker-tape), on tape, or on computer disk. Recorded information can then be used to compile a history of changes in thickness of floating liquid 20. A second source of compressed air 34, is connected to sensor 32 via mechanical fitting 18.

Bubbler hole 28 is connected, via conduit 30, to a pneumatic pressure sensor 32. Sensor 32 measures back pressure and actuates a valve that controls air flow to other pneumatically controlled devices. Such a sensing device is called a diaphragm amplifier and is manufactured by several companies. Examples are Norgren in Littleton, Colo., its part number is 5DA-010-DOA: Festo in Hauppauge, N.Y., its part numbers are 7319VL-3-0,9-N0,5 and 7520 VL-3-4-N-5. These amplifiers can be connected in series to increase their back pressure sensitivity and their resulting relay pressure which can be used to actuate other pneumatic devices, e.g. a signaling device 36.

Compressed air 33, e.g., at 7 to 21 kilo-Pascals (kPa) (1 to 3 pounds per square inch gage pressure (psig)) enters pneumatic sensor 32 through tee 25, where it is directed, via conduit 30 to bubbler hole 28. In addition, compressed air 34 can also be directed from sensor 32 via conduit 38 to other devices, such as signaling device 36. Device 36 may be a visual or an audible indicator.

If additional floating liquid 20, e.g., oil, is added to the surface of the submerged liquid, e.g., from drainage from soil, or the addition of oil to a holding pond from refinery operations, the thickness of floating liquid 20 increases. As floating liquid 20 increases in thickness, its surface rises further above float 26 and bubbler hole 28. I.e., float 26 submerges in liquid 20. This causes the pressure at bubbler hole 28 to increase. I.e., the pressure at bubbler hole 28 changes in proportion to the thickness of floating liquid 20. The back pressure at bubbler hole 28 is transferred to pressure sensor 32 via conduit 30. Therefore, the pressure at bubbler hole 28 can be sensed by pressure sensor 32. After detecting a predetermined pressure, sensor 32 can actuate a valve that allows compressed air 24 to flow into conduit 38. Compressed air 34 flowing through conduit 38 powers a device that performs a desired function, i.e., operate signaling device 36 or is directed to a recording device 37.

Bubbler hole 28 can be located at any depth along float 26. If bubbler hole 28 is located just above submerged liquid-air interface 22–24 when no floating liquid 20 is present, the back pressure at pressure sensor 32 will correspond only to the thickness of the floating liquid 20. Pressure sensor 32 can be adjusted to sense as little as 0.125 inch of water pressure (e.g. 25 Pa (0.0036 psig)) and thus activate a remote device, e.g., signaling device 36.

Alternatively, rather than communicating with floating liquid 20, bubbler hole 28 may be positioned to communicate with liquid 22 or air 24. If bubbler hole 28 communicates with liquid 22, and the purpose of the device is to measure or indicate the presence of only floating liquid 20, the actuating pressure of pressure sensor 32 must be greater than if bubbler hole 28 communicates only with floating liquid 20. This increased actuating pressure is due to the additional thickness of liquid 22 above bubbler hole 28. If bubbler hole 28 is located at a point on float 26 significantly above submerged liquid-air interface 22–24 when no floating liquid 20 is present, a greater amount of floating liquid 20 is necessary to immerse bubbler hole 28 and have sensor 28 to detect floating liquid 20. In this case, the back pressure felt by pressure sensor 32 will not be determined by the total thickness of floating liquid 20, but rather only to the thickness of liquid 20 above bubbler hole 28.

Figure 2:
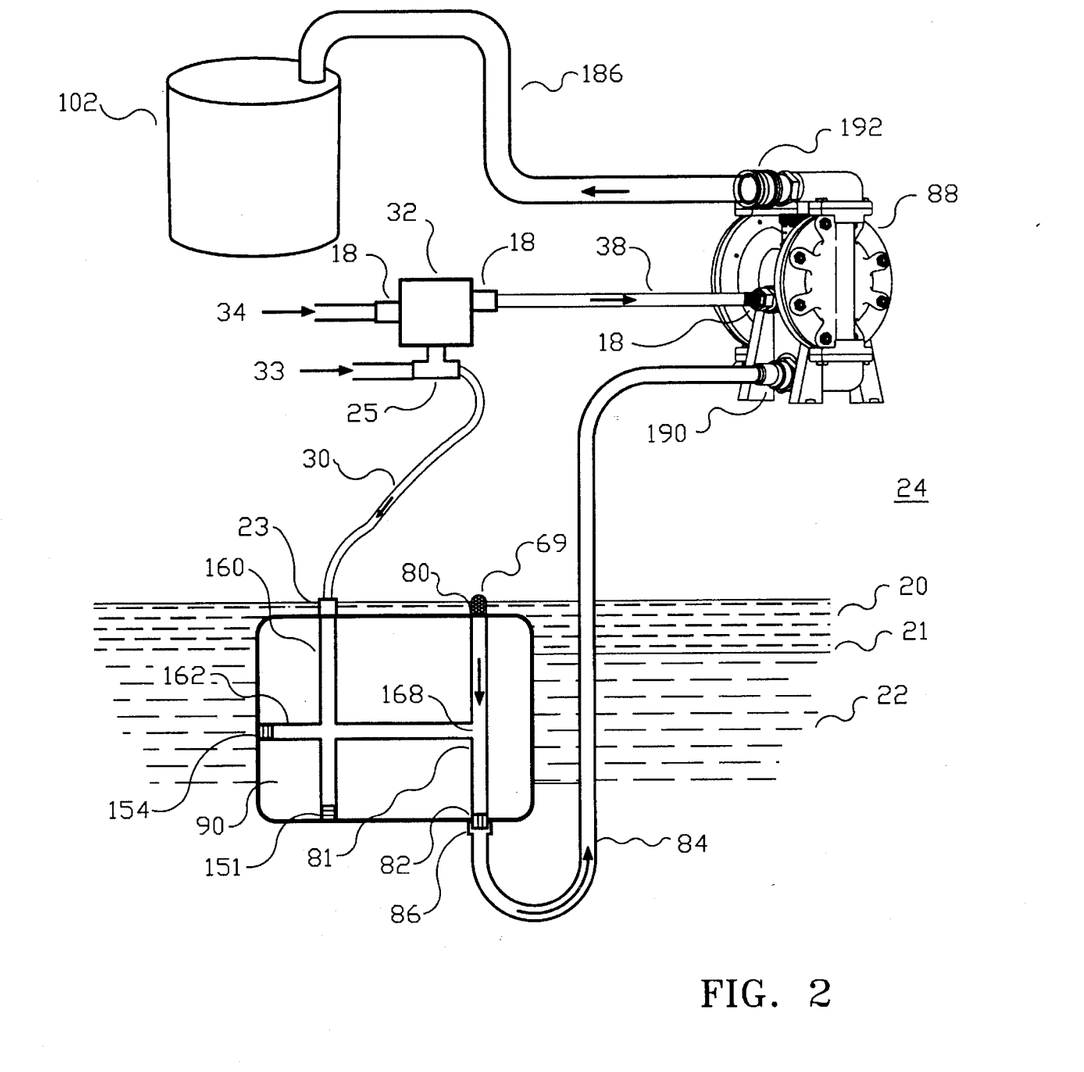
FIG. 2 shows a diagram of a combination floating liquid detection and recovery device that operates on the principle of specific gravity, in accordance with another embodiment of the invention and having a bubbler hole-floating liquid interface internal to the recovery float.

FIG. 2—SPECIFIC GRAVITY TYPE FLOATING LIQUID DETECTION AND SKIMMING DEVICE

FIG. 2 shows the device of FIG. 1 coupled with a specific gravity type floating liquid skimming device. Bubbler hole 168 is formed internally to the floating recovery unit 90 of the skimming device and a pump 88 is connected to sensor 32 via conduit 38 and mechanical fittings 18. Pump 88 is activated by high pressure air, e.g., 414 kPa (60 psig), released into conduit 38 by sensor 32 in response to sensing a predetermined pressure, e.g., 24.8 Pa gage pressure (0.0036 psig).

Recovery unit 90 is a float with vertical bore holes 81 and 160 and a horizontal conduit 162. Bore hole 81 has an inlet 80 at the uppermost portion of the recovery unit 90 and an outlet 82 at the lowermost portion of recovery unit 90. Outlet 82 is connected to a discharge conduit 84 via a check valve 86. Check valve 86 allows recovered liquid 20 to flow only out of recovery unit 90. (Check valve 86 also functions as a mechanical fitting.) Discharge conduit 84 is connected to pump 88 via a mechanical fitting 190. Discharge conduit 84 is sufficiently flexible to allow the recovery unit 90 to follow vertical changes in the surface of the submerged fluid 22 unhindered. The outlet of pump 88 is connected to a remote fluid receiver 102 via a conduit 186 and a mechanical fitting 192. Conduit 162 in the lower portion of recovery unit 90 connects vertical bore holes 160 and 81. At the intersection of conduit 162 and bore hole 81 is a bubbler hole 168. Vertical bore hole 160 has a mechanical fitting 152 which plugs the bottom of bore hole 160, preventing the passage of air and liquids. Vertical bore hole 160 has another mechanical fitting 151 at the top of hole 160. Mechanical fitting 23 connects conduit 30 to bore hole 160.

Recovery unit 90 operates on the principle of specific gravity, e.g., floats on submerged liquid 22 and sinks in liquid 20; therefore, recovery unit 90 floats at two-liquid interface 21. Recovery unit 90 floats freely and follows the vertical level changes of two-liquid interface 21. When sufficient thickness of liquid 20 exists, the uppermost portion of recovery device 90 will submerge in liquid 20, thereby allowing liquid 20 to enter inlet 80 through screen 69 and collect in conduit 84 and bore hole 81. As liquid 20 continues to flow into inlet 80, it fills bore 81 above bubbler hole 168. Discharge conduit 84 is sufficiently flexible to allow the recovery unit 90 to follow vertical changes in the surface of the submerged fluid 22 unhindered.

The detection system performs as disclosed in the description of FIG. 1 with the exception that the back pressure at bubbler hole 168 is caused by floating liquid 20 that has entered inlet 80 and has collected and risen in bore 81. At a predetermined pressure, sensor 32 activates pump 88 which then draws liquid 20 from recovery unit 90 via a conduit 84. Liquid 20 is directed from pump 88 to fluid receiver 102 via conduit 186. When sufficient liquid 20 is removed from bore 81, the level in bore 81 drops and thus the backpressure detected at bubbler 168 decreases below the level which activates sensor 32. This causes sensor 32 to shut off pump 88. Thus the system automatically recovers floating liquid 20. Additional information on skimming devices that operate on the principle of specific gravity is disclosed in my aforementioned U.S. Pat. Nos. 4,663,037 and 4,761,225.

Figures 3, 3A, 3B:
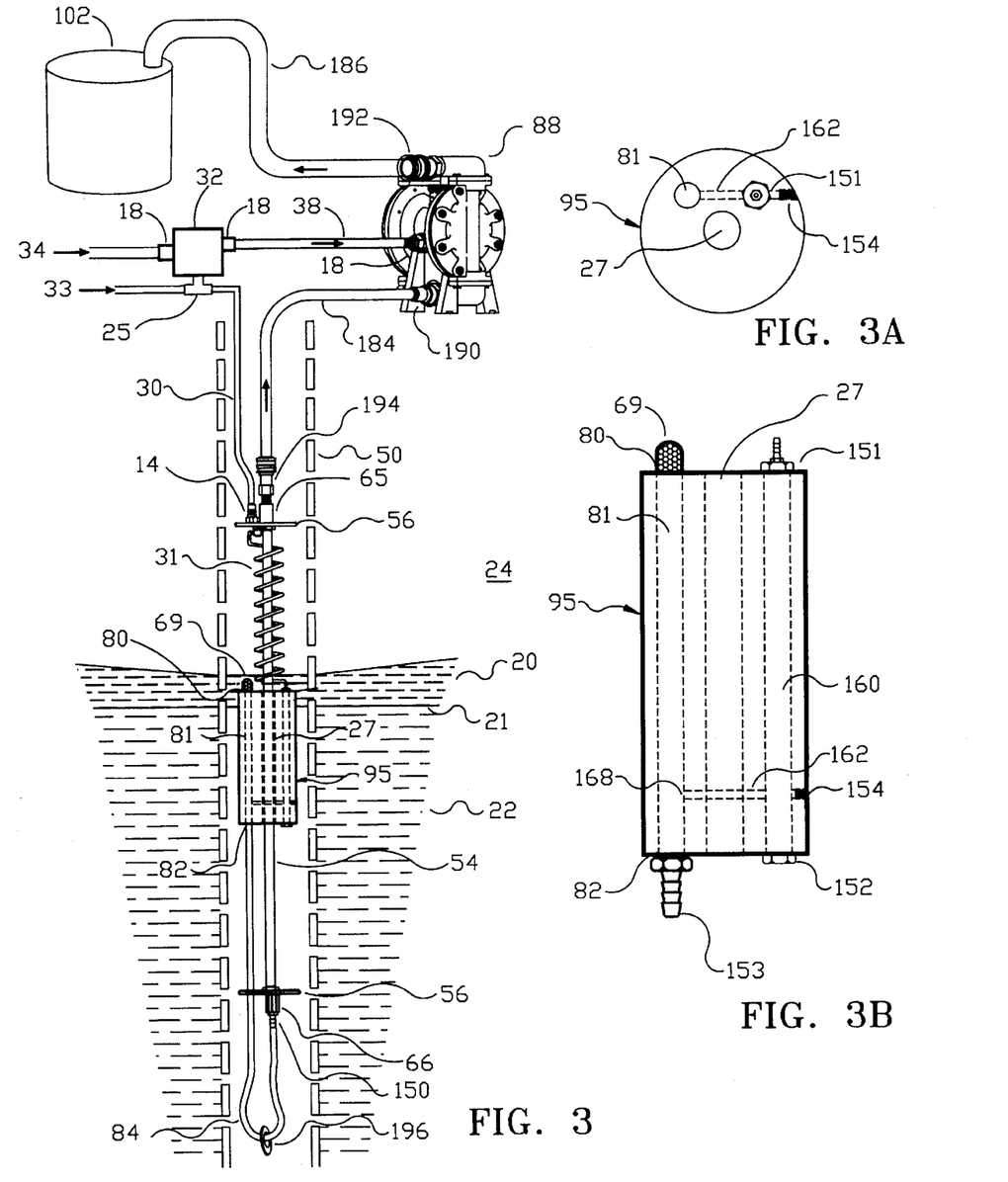

FIG. 3, FIG. 3-A, AND FIG. 3-B—A SPECIFIC GRAVITY TYPE FLOATING LIQUID DETECTION AND SKIMMING DEVICE WHICH UTILIZES A BUBBLER HOLE INTERNAL TO THE DEVICE AND IS ADAPTED FOR USE INSIDE A WELL CASING.

FIGS. 3, 3-A, and 3-B show another version of a specific gravity type floating liquid detection and skimming device. The apparatus shown in FIGS. 3, 3-A, and 3-B operates as described in FIG. 2. The primary difference is that recovery unit 95 slides along conduit 54, which operates as a guide to maintain the recovery float unit 95 vertical and away from the walls of a well casing 50.

Float 95 has all of the components mentioned in the description of FIG. 2, plus a rigid conduit 54 and two disk spacers 56. One disk spacer 56 is attached to the upper end of rigid conduit 54 via mechanical fitting 64. The other disk spacer 56 is attached to the lower end of rigid conduit 54 via another mechanical fitting 64. A float 95, modified from float 26 shown in FIGS. 1 and 2, fits into well casing 50. Rigid conduit 54 also serves a passageway for transporting recovered liquid 20 out of well casing 50.

Rigid conduit 54 runs through bore hole 27. A flexible conduit 31 is coiled around rigid conduit 54. One end of flexible conduit 31 is connected to conduit 30 via a mechanical fitting 14. The other end of flexible conduit 31 is connected to bore 160 via mechanical fitting 151. Disk spacers 56 have diameters smaller than well casing 50 and larger than float 58 and are located at opposite ends of conduit 54. Disk spacers 56 center rigid conduit 54 within the well casing. Rigid conduit 54 guides float 27 inside well casing 50. Flexible coiled conduit 31 provides a flexible and durable passageway for air to travel from pressure sensor 32 to bore 160. It does not restrict or interfere with movement of float 95.

Recovery unit 95 has three vertical bore holes 81, 27, 160; bore hole 81 receives the floating liquid, bore hole 27 guides recovery unit along rigid conduit 54, and bore hole 160 passes compressed air used for measuring back-pressure. A conduit 162 in the lower portion of recovery unit 95 connects vertical bore holes 160 and 81. At the intersection of conduit 162 and bore hole 81 is a bubbler hole 168. Vertical bore hole 160 has a mechanical fitting 152 which plugs the bottom of bore hole 160, preventing the passage of air and liquids. Vertical bore hole 160 has another mechanical fitting 151 at the top of hole 160. Mechanical fitting 151 connects conduit 31 to bore hole 160.

In FIG. 3, as compared to FIG. 2, rather than connecting recovery unit 95 directly with pump 88, discharge conduit 84 connects recovery unit 95 to conduit 54 via a mechanical fitting 150 and a check valve 66. Mechanical fitting 153 connects conduit 84 to check valve 66 which is connected to rigid conduit 54 and secures disk 56 to the same. Rigid conduit 54 is connected to conduit 184 via a mechanical fitting 65 and another mechanical fitting 194. Mechanical fitting 65 connects rigid conduit 54 to mechanical fitting 194 and also secures disk spacer 56 to conduit 54. Mechanical fitting 194 connects mechanical fitting 65 (and hence conduit 54) to conduit 184. Conduit 184 is connected to inlet of pump 88 via mechanical fitting 190, as shown in FIG. 2. A weight 84 slides freely along conduit 84 and keeps the same taut, thus preventing conduit 84 from becoming entangled.

Bubbler hole 168 is connected, via conduits 30 and 31, bore hole 160, and conduit 162, to pneumatic pressure sensor 32. Sensor 32 senses back pressure and, upon sensing a predetermined pressure, actuates a valve that controls air flow to other pneumatically controlled devices. Compressed air 33 enters conduit 30 via tee 25 and passes through conduit 31, bore hole 160, and conduit 162, to hole 168. In turn, hole 168 emits the air into bore hole 81.

As floating liquid 20 increases in thickness, its surface rises above recovery unit 95. When the surface of floating liquid 20 is above the top of recovery unit 95, liquid 20 flows into inlet 80. Liquid 20 continues entering recovery unit 95 and collects in conduits 54 and 84 and bore hole 81. When liquid 20 fills recovery unit 95, i.e., collects in conduits 54 and 84 and fills bore hole 81, its surface resides above bubbler hole 168, e.g., 15.2 cm (6 inches) above hole 168. This increased thickness creates a back pressure at bubbler hole 168. The back-pressure at hole 168 is transferred to pressure sensor 32.

When sensor 32 detects a predetermined pressure, e.g., 1200 Pa gage pressure (0.174 psig), it releases high pressure air, e.g., 414 kPa gage pressure (60 psig), into conduit 38. The high pressure air powers a pneumatic pump 88 which draws collected liquid 20 from recovery unit 95 and pushes it to liquid receiver 102.

One of the advantages to this arrangement is that recovery unit 95 does not require a sensor 32 as sensitive as one required to detect only 0.125 inches of floating liquid 20 for removing floating liquid 20 in well casing 50 down to a very thin layer. Usually a sensor 32 which can detect down to 0.125 inches of water column (25 Pa (0.0036 psig)) is more expensive and more prone to malfunction than a sensor 32 which is actuated by 3 or more inches of water pressure (600 Pa (0.086 psig)). Thus this arrangement can be less expensive and more reliable.

Figure 4:
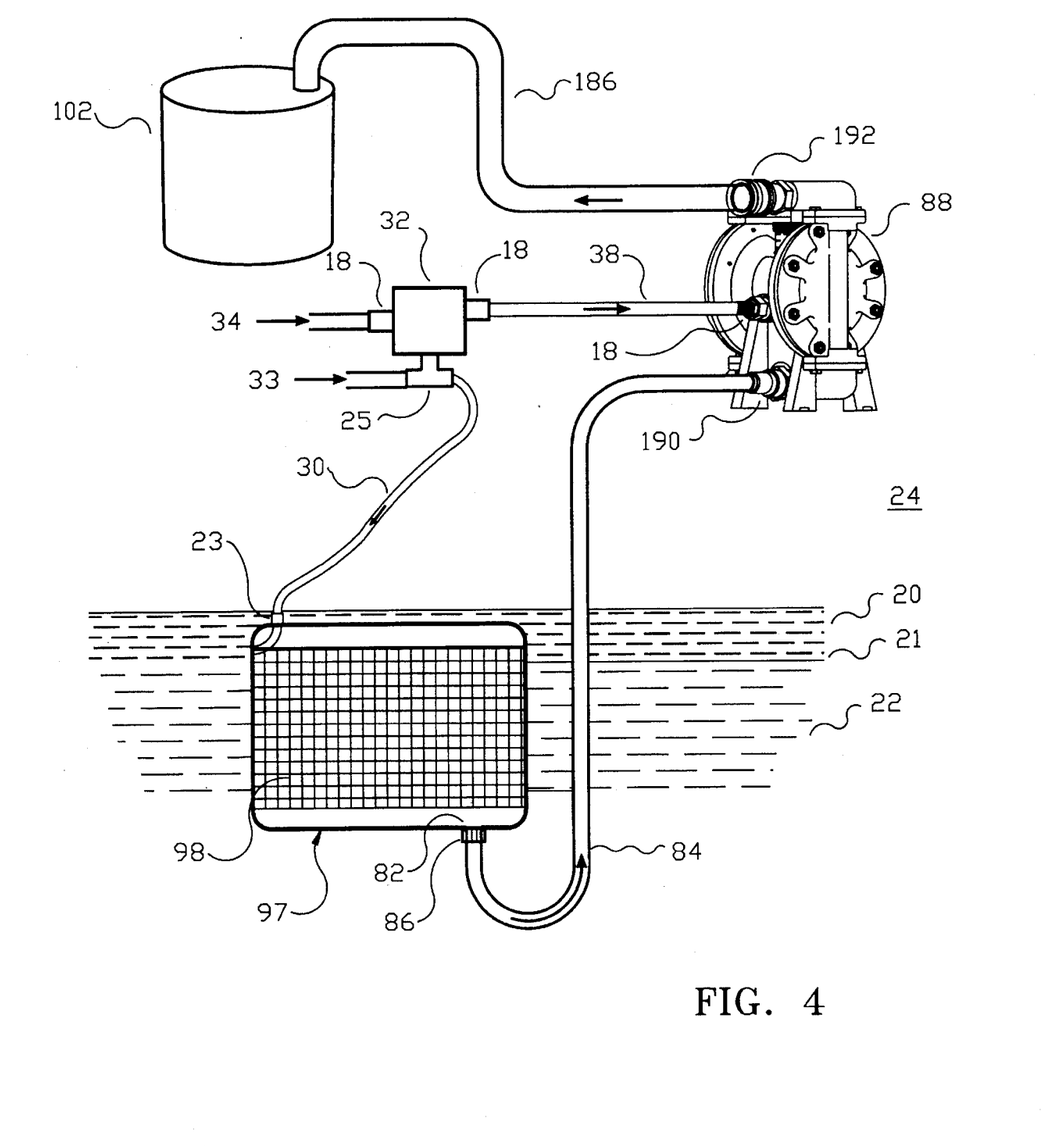
FIG. 4 shows a combination floating liquid detection and recovery device which uses a semipermeable membrane, in accordance with the invention.

FIG. 4—SELECTIVE MEMBRANE TYPE DETECTION AND SKIMMING DEVICE

Figures 5, 5A:
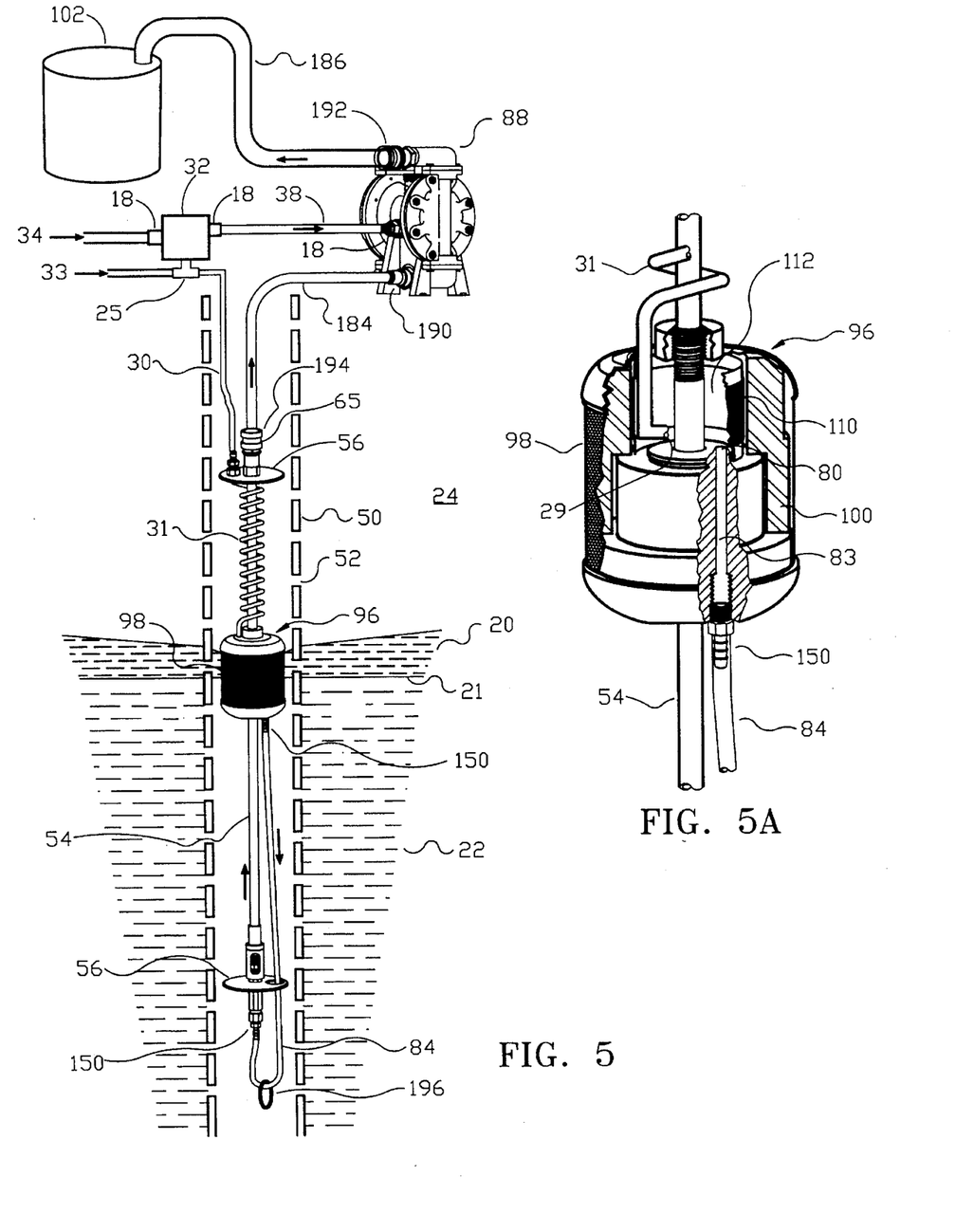
Figure 5:
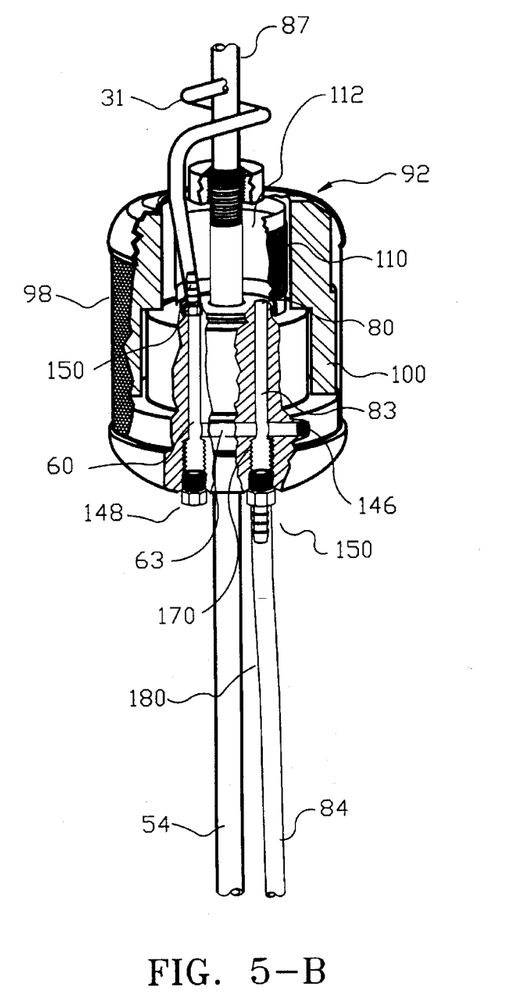
FIG. 5 shows a device similar to FIG. 4, but which is adapted for use inside a well casing and having a bubbler hole-floating liquid interface internal to the semipermeable screen.

FIG. 4 shows the detection and recovery device of FIG. 2 coupled with a selective membrane skimming device, e.g., one which incorporates a semi-permeable membrane. The detection and recovery device is constructed as shown in FIG. 2; however, instead of coupling the detection device with a specific gravity type skimming device, e.g., specific gravity recovery unit 90, the detection device is coupled with a skimming device that incorporates a semipermeable membrane, e.g., a semipermeable membrane recovery unit 97. A bubbler hole 29 can be attached outside of recovery unit 97 or placed inside, as shown in FIG. 5-A. The selective membrane type detector and skimmer shown in FIG. 4 has bubbler hole 29 located inside recovery unit 97. When positioned inside recovery unit 97, hole 29 is in a fluid collection chamber 112 surrounded by a selectively permeable membrane 110 as shown in FIG. 5-A. Selective membrane 110 allows floating liquid 20 to pass therethrough, but prevents the passage of submerged liquid 22. An example of this type of membrane is one that allows the passage of non-polarized molecules, such as liquid hydrocarbon molecules, while restricting the passage of polarized molecules, such as water molecules. It is also possible to use this device to recover the submerged liquid 22. An example of this is if the submerged liquid 22 was an oil that was heavier than water. The selective membrane 110 would then allow submerged liquid 22 to pass therethrough, but prevent the passage of floating liquid 20. A bore hole 83, which provides an outlet for captured liquids, connects fluid collection chamber 112 to discharge conduit 84 via check valve 86. As shown in FIG. 2, conduit 84 is connected to pump 88.

Recovery unit 97 has an average specific gravity such that its selective membrane 110 floats at the submerged liquid-air interface 22–24 when no floating liquid 20 is present and fluid collection chamber 112 is either empty or full. By floating in this way, recovery unit 97 is able to remove floating liquid 20 down to the surface of the submerged liquid 22. Recovery unit 97 never resides below liquid interface 21. Sometimes, such as when the floating liquid has a large thickness and fluid collection chamber 112 is empty, recovery unit 97 may reside above interface 21. Sensor 32 communicates with bubbler hole 29 and is connected to a pumping device 88.

When bubbler hole 29 is located outside selective membrane 110, the sensing portion of the detection unit performs in a manner similar to the one described in FIG. 1.

When bubbler hole 29 is located inside chamber 112, it will become immersed only in liquid 20. Again, the pressure at hole 29 increases as the thickness of liquid inside the chamber 20 increases.

At a predetermined pressure above atmospheric pressure, e.g., 25 Pa gage pressure (0.0036 psig), at bubbler hole 29, sensor 32 activates pump 88 which in turn moves liquid 20 away from recovery unit 97.

Additional information on skimming devices that use a selective membrane is disclosed in my aforementioned U.S. Pat. No. 4,497,370.

FIG. 5 AND FIG. 5-A—SELECTIVE MEMBRANE TYPE DETECTION AND SKIMMING DEVICES FOR USE IN A WELL CASING

FIGS. 5 and 5-A show the detection and recovery device of FIG. 2 coupled with a selective skimming device adapted for well environments. The down-well guide system for this device operates the same as the system described in FIG. 3. Bubbler hole 29 can be located outside recovery unit 96 or placed inside, as shown in FIG. 5-A. In the selective membrane type detector and skimmer of FIG. 5, bubbler hole 29 is located inside recovery unit 96 and is adapted for use inside well casing 50. When positioned inside recovery unit 96, hole 29 is in fluid collection chamber 112 which is surrounded by a selective permeable membrane 110. Membrane 110 allows floating liquid 20 to pass therethrough, but prevents the passage of submerged liquid 22. An example of this type of membrane is one that allows the passage of non-polarized molecules, such as liquid hydrocarbon molecules, while restricting the passage of polarized molecules, such as water molecules.

Recovery unit 96 has an average specific gravity such that its selective membrane 110 floats at interface 22–24 when no liquid 20 is present and fluid collection chamber 112 is either empty or full. By floating in this way, unit 96 is able to remove liquid 20 down to the surface of liquid 22. Unit 96 never resides below interface 21. Sometimes, such as when floating liquid 20 has a large dimensional thickness and fluid collection chamber 112 is empty, recovery unit 96 may reside above interface 21. Sensor 32 communicates with hole 29 and is connected to pumping device 88.

When hole 29 is located outside membrane 110, the sensing portion of the detection unit performs in a manner similar to the one described in FIG. 1.

When hole 29 is located inside chamber 112, it will become immersed in only liquid 20. Again, the pressure at hole 29 increases as the thickness of liquid inside chamber 20 increases. At a predetermined pressure above atmospheric pressure (e.g., 25 Pa gage pressure (0.0036 psig)) at bubbler hole 29, sensor 32 activates pump 88 which in turn moves liquid 20 from recovery unit 96.

FIG. 5-B—SELECTIVE MEMBRANE TYPE DETECTION AND SKIMMING DEVICE FOR USE IN A WELL CASING WITH BUBBLER HOLE BELOW THE SELECTIVE MEMBRANE HOUSING

FIG. 5-B shows another version of a selective membrane type floating liquid detection and recovery device. This version is similar to the device shown in FIGS. 5 and 5-A. However, rather than communicating with floating liquid 20 internal to housing 112 formed by selective membrane 110 as shown in FIG. 5-A, a bubbler hole 170 communicates with liquid 20 after it is captured by a recovery unit 92 and held in conduit 83 below the housing 112. The recovery device shown in FIG. 5-B can take the place of recovery unit 96 shown in FIG. 5.

Pressure sensor 32 and conduits 30 and 31 are connected as described in FIG. 3. Recovery unit 92 has all the components as shown for recovery unit 96 of FIG. 5-A. In addition, recovery unit 92 has a second vertical bore hole 60 and an internal conduit 63. The upper portion of bore hole 60 is connected to conduit 31 via mechanical fitting 150. The lower portion if bore hole 170 is plugged by a mechanical fitting 148, thus preventing the passage of air or liquid. One end of conduit 63 is open to bore hole 170 while the other end of conduit 63 is plugged by a mechanical fitting 146. Additionally, conduit 63 intersects bore hole 83. Thus conduit 63 connects bore hole 60 with bore hole 83. A bubbler hole 170 is located at the interface of conduit 63 and bore hole 83.

When liquid 20 passes through selective membrane 110 and fills recovery unit 92, i.e., collects in conduit 83 and resides in chamber 112, its surface resides above bubbler hole 170, e.g., 10 cm (4 inches).

The thickness of liquid 20 between hole 170 and the surface of the liquid 20 inside chamber 112 creates pressure at hole 180. The back-pressure at hole 170 is transferred to sensor 32 via conduits 30 and 31. When sensor 32 detects a predetermined pressure, e.g., 640 Pa gage pressure (0.092 psig), it releases high pressure air, e.g., 414 kPa gage pressure (60 psig), into conduit 38. This air powers a pneumatic pump 88 which draws collected liquid 20 from the well and pushes it to liquid receiver 102.

FIG. 5-C—SELECTIVE MEMBRANE TYPE DETECTION AND SKIMMING DEVICE FOR USE IN A WELL CASING WITH BUBBLER HOLE BELOW THE RECOVERY UNIT

Another way of accomplishing the same result is shown in FIG. 5-C. Conduit 31 is connected to bore hole 60 via mechanical fitting 150. Conduit 62 is connected to bore hole 60 via another mechanical fitting 150. Conduit 62 is connected to a hollow tee fitting 182 via mechanical fitting 154. Bore hole 83 is connected to conduit 84 via mechanical fitting 150. Tee fitting 182 is inserted into conduit 84; it is connected to conduit 84 via mechanical fittings 150. Thus tee fitting 182 connects conduits 62 and 84. A bubbler hole 180 is thereby created inside the tee fitting 180.

Recovery units of FIGS. 5-B and 5-C, which are used in the detection and recovery device of FIG. 5, allow a greater amount of trapped floating liquid 20 to reside above their respective bubbler holes 170 and 180 than the device of FIG. 5-A for a given thickness of liquid 20 inside well casing 50. The greater thickness of floating liquid 20 corresponds to a greater pressure; thus, when the detection and recovery device of FIG. 5 incorporates either of the recovery units of FIGS. 5-B and 5-C, it requires a less sensitive sensor 32 than when it incorporates the recovery unit of FIG. 5-A for a given thickness of floating liquid 20 inside the well casing. Alternatively, for a given sensitivity of sensor 32, the detection and recovery device of FIG. 5 using the recovery unit of FIG. 5-B or FIG. 5-C can actuate pumping unit 88 when less liquid 20 resides in the well casing than when using the recovery unit of FIG. 5-A.

One of the advantages to this arrangement is that the recovery units of FIGS. 5-B and 5-C do not require a sensor 32 as sensitive as one required to detect only 0.125 inches of floating liquid 20 (25 Pa (0.0036 psig) to remove floating liquid 20 in the well 50 down to a very thin layer. Usually a sensor 32 which can detect down to 0.125 inches of water column is more expensive and more prone to malfunction than a sensor 32 which is actuated by 3 or more inches of water pressure. Thus this arrangement can be less expensive and more reliable.

CONCLUSION, RAMIFICATIONS AND SCOPE OF INVENTION

The reader will see that the pneumatically powered floating liquid detection and recording device described has environmental, safety, and economic advantages. It is easy to transport and install, even for well applications. It has flexibility of design which allows it to be easily and economically installed; for example, the design permits use in existing monitoring wells, i.e., wells used for monitoring underground liquids, rather than requiring newly drilled wells. This device is easy to operate; it requires no operator supervision. It positions itself automatically within the fluid mixture and can operate properly, regardless of fluid level fluctuations. In addition, it operates continuously without interruption and requires little maintenance; it does not need to be removed from its testing site for emptying, cleaning, or replacing fluid collection chambers. It can also automatically actuate other devices (e.g., signaling devices) at a predetermined floating liquid thickness. Furthermore, it does not require any electrical parts, thus eliminating the possibility of fire or explosion due to electronic circuitry. Its design is simple and very versatile; areas of application include small and large diameter wells, ditches, tanks, vats, vessels, harbors, lakes, reservoirs, ponds, lagoons, rivers, streams and the like. It can also be coupled to a timing device so that it will operate periodically only.

Coupled with a skimming device, the present device also recovers the detected floating liquid. The combination floating liquid detection and recovery unit has all the advantages of the aforementioned detection unit as well as its own advantages which are discussed below.

When coupled with a skimming device, the detection device controls the recovery unit; it insures that the fluid recovery pump only operates when floating liquids are present. Thus the detection device provides recovery units with new advantages. The primary advantage occurs when the skimming device is located in a contained space with harmful vapors, such as a well casing or storage tank with hydrocarbon vapors. By pumping only when floating liquid is present, the amount of harmful vapors expelled into the atmosphere is minimized. A second advantage is an overall increase in the system's energy efficiency gained by operating the pumping unit only when fluid is present. This increase in efficiency can allow more pumping units to operate from a single compressed air source, or it can increase the length of time that a skimming unit can operate on a limited air source, e.g., a tank of compressed air. A third advantage is an increase in pump life by eliminating unnecessary wear and tear.

Although the aforementioned description provides numerous specific details, it should not be interpreted in such a narrow sense; instead, the details should be viewed as examples of several preferred embodiments rather than as constraints. Many other variations exist. For example, the device can use different types of conduit and conduit configurations, such as wrapping one conduit around another conduit, letting either conduit move freely, or loading the detection conduit on a feed and retract mechanism. Float and recovery unit guide systems can vary as well, e.g., a perforated tubing can house the float, a conduit can run through a bore hole in the float, or a plurality of rigid conduits can form a cage around the float wherein the conduits guide the float. Also, different types of floats, such as air or fluid filled floats, differently shaped floats, floats with stabilizers, or floats made of different materials can be used. Other variations include different kinds of pumping devices, such as bladder pumps, diaphragm pumps, axial flow pumps, pneumatic ejector pumps, axial flow pumps, centrifugal pumps, horizontal split case pumps, and capillary pumps. The pump can also be located elsewhere; it can reside inside or outside well casings, above or below the recovery device, and in or out of the liquids. The bubbler hole can alternatively be located on the recovery device, in the recovery device, or in the fluid receiving conduit below the recovery device. Furthermore, bubbler holes can open to either the floating liquid, the submerged liquid, or to the air. The detection device is not limited to actuating pumping devices; it can also be used to actuate other mechanisms, such as signaling devices, visual monitoring systems, and mixing devices.

Thus the scope of the invention should be determined by the claims and their legal equivalents, rather than by the examples illustrated and described.

What is claimed is:

1. In a sump having varying surface fluid levels, apparatus for detecting a first fluid of given specific density within a recovery unit, the apparatus comprising:

a recovery unit adapted for floating within the sump at the varying surface fluid levels having a specific gravity greater than the given specific density but less than a higher specific density of a second fluid layer whereby the recovery unit floats on the second fluid having the higher specific density at the interface between the first fluid layer and the second fluid layer;

means on the recovery unit for receiving fluid from the first fluid layer;

an air source;

a bubbler hole defined within the recovery unit for discharging air within the recovery unit at least below a surface of the first fluid accumulated within the recovery unit;

a conduit communicated from the air source to the recovery unit at the bubbler hole for discharging air from the bubbler hole through at least a portion of the first fluid layer;

means for measuring back pressure in the conduit between the air source and bubbler hole to determine thickness of the first fluid layer above the bubbler hole; and, means for pumping the first fluid from the recovery unit responsive to the means for measuring back pressure in the conduit.

2. In a sump having varying surface fluid levels, apparatus for detecting a first fluid of given specific density within a recovery unit according to claim 1 and further comprising:

means for tethering the recovery unit in a limited up and down motion with respect to the sump.

3. In a sump having varying surface fluid levels, apparatus for detecting a first fluid of given specific density within a recovery unit according to claim 1 and further comprising:

means for blocking entry of debris from the sump to the recovery unit.

4. In a sump having varying surface fluid levels, apparatus for detecting a first fluid of given specific density within a recovery unit according to claim 1 and further comprising:

means for permitting entry of only said first fluid into the recovery unit.

5. In a sump having varying surface fluid levels, a method for detecting a first fluid layer of a first fluid of given specific density gathered from an interface with a second fluid having a higher specific density, comprising the steps of:

providing a recovery unit for floating within the sump at the varying surface fluid levels having a specific gravity greater than the given specific density but less than the higher specific density whereby the recovery unit floats on the second fluid having the higher specific density at the interface between the first fluid layer and the second fluid layer;

floating said recovery unit on the surface of the sump;

providing means on the recovery unit for receiving fluid from the first fluid layer;

providing an air source;

providing a bubbler hole defined within the recovery unit for discharging air within the recovery unit at least below a surface of the first fluid accumulated within the recovery unit;

communicating air from the air source to the recovery unit at the bubbler hole for discharging air from the bubbler hole through at least a portion of the first fluid layer;

measuring back pressure in the conduit between the air source and bubbler hole to determine thickness of the first fluid layer above the bubbler hole; and, pumping the first fluid from the recovery unit responsive to the measuring of back pressure in the conduit.

6. In a sump having varying surface fluid levels, a method for detecting a first fluid layer of a first fluid of given specific density gathered from an interface with a second fluid having a higher specific density according to the steps of claim 5 and further including:

tethering the recovery unit in a limited up and down motion with respect to the sump.

7. In a sump having varying surface fluid levels, a method for detecting a first fluid layer of a first fluid of given specific density gathered from an interface with a second fluid having a higher specific density according to the steps of claim 5 and further including:

blocking entry of debris from the sump to the recovery unit.

8. In a sump having varying surface fluid levels, a method for detecting a first fluid layer of a first fluid of given specific density gathered from an interface with a second fluid having a higher specific density according to the steps of claim 5 and further including:

permitting entry of only said first fluid into the recovery unit.

* * * * *